United States Patent [19]

Kitamura et al.

[11] Patent Number: 4,976,540
[45] Date of Patent: Dec. 11, 1990

[54] METHOD FOR DETECTING COLORED FOREIGN PARTICLES IN LIGHT-COLORED POWDER AND SYSTEM THEREFOR

[75] Inventors: Hajime Kitamura, Chiba; Masaru Takeuchi; Hideo Yoshikoshi, both of Ibaraki, all of Japan

[73] Assignee: Shin-Etsu Chemical Co., Ltd., Tokyo, Japan

[21] Appl. No.: 357,335

[22] Filed: May 25, 1989

[30] Foreign Application Priority Data

May 27, 1988 [JP] Japan .................................. 63-129857

[51] Int. Cl.$^5$ ..................... G01N 21/28; G01N 21/85; G01N 21/89
[52] U.S. Cl. .................................. 356/38; 356/237; 356/445
[58] Field of Search ................... 356/36, 38, 237, 445

[56] References Cited

U.S. PATENT DOCUMENTS 3,549,263 12/1970 Osawa et al. .................. 356/237 X Primary Examiner—Vincent P. McGraw
Attorney, Agent, or Firm—McAulay Fisher Nissen & Goldberg

[57] ABSTRACT

An efficient and reliable method and a system are proposed for detecting colored foreign particles in a white or light-colored powdery product such as a polyvinyl chloride resin with an object of product inspection and quality control. The method comprises the steps of eliminating static electricity from the powder, e.g., by spraying ethyl alcohol, continuously feeding the powder at a controlled rate on to a belt conveyor to form a uniform powder layer having a flat and even surface thereon, bringing the powder layer below a reflection-type laser-beam scanning detector projecting a laser beam with scanning and receiving the reflected beam and monitoring the output signals coming out of the detector.

6 Claims, 1 Drawing Sheet

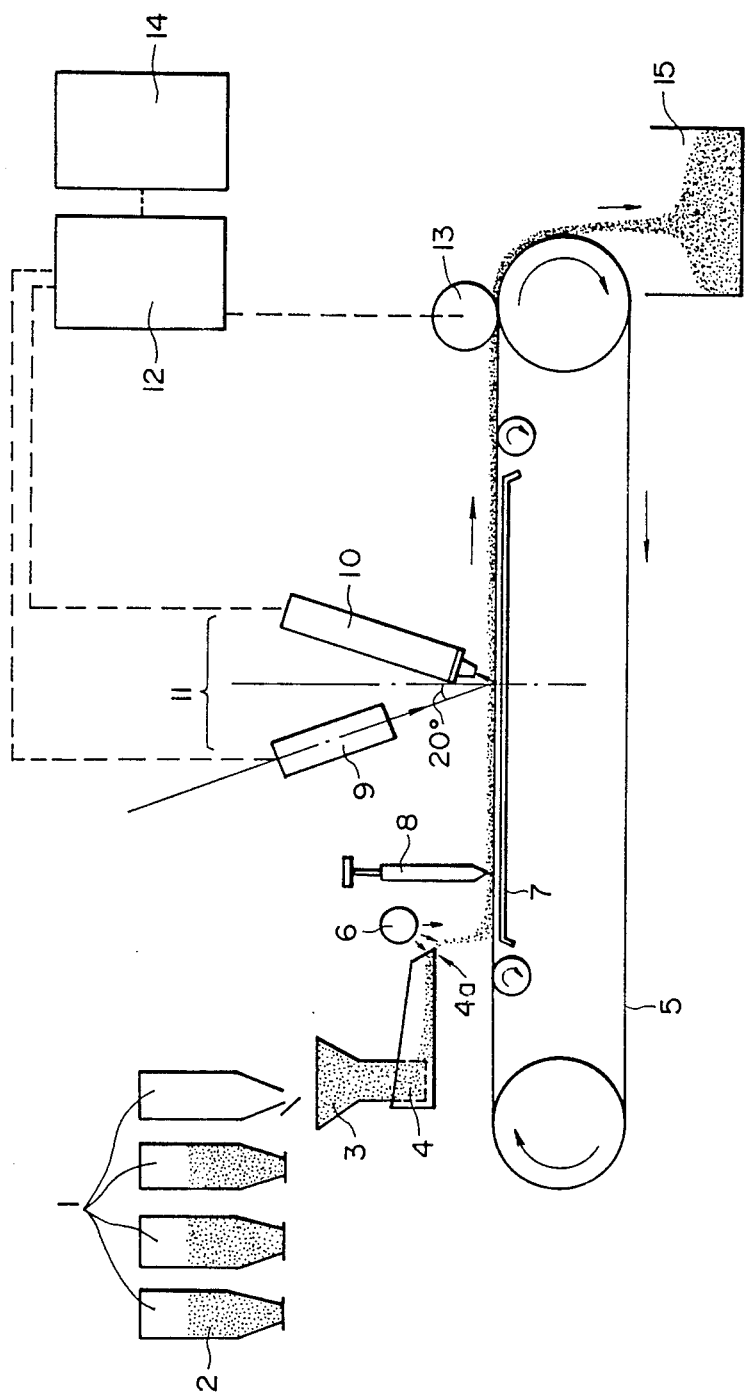
FIGURE

METHOD FOR DETECTING COLORED FOREIGN PARTICLES IN LIGHT-COLORED POWDER AND SYSTEM THEREFOR

BACKGROUND OF THE INVENTION

The present invention relates to a method for detecting colored foreign particles in a white or light-colored powder and a system therefor. More particularly, the invention relates to a method for detecting colored foreign particles in a white or light-colored powder, such as a powder of a synthetic resin, e.g., polyvinyl chloride, in a continuous process with an object of process control and quality control in order to feed the results of detection back to the production line as well as to a system for practicing the method.

As is well known, synthetic resins such as polyvinyl chloride are widely used as a material for manufacturing various kinds of shaped articles such as sheets, films, decorative boards, containers and so on used for wrapping of food, clothings and the like as well as parts of electric and electronic appliances. It is a recent trend in these applications that the resin powder is desired to contain colored foreign particles as small as possible in number to comply with the demand for shaped articles of higher and higher quality and commercial value. Foreign particles intermixed in the resin powder are very detrimental on the quality of the final products not only in the appearance but also in their practical performance to cause incomplete printing thereon and decrease in the mechanical strengths thereof leading to fissures and cracks formed in the shaped articles.

Accordingly, it is usual in the production plants of such a resin in a powdery form to undertake a step of quality inspection to detect such colored foreign particles among other various items of inspection required before shipping of the product to discard a lot of the product containing such colored foreign particles in excess of a certain tolerable quality control level in number. Conventional methods undertaken for such a purpose are mostly conducted by visual inspection and picking up of the foreign particles by manual works although a proposal has been made for a method by using an instrument such as stroboscope to conduct image analysis while such an instrumental method is practiced only in a limited number of production lines.

Needless to say, the results of a visual inspection, which inherently cannot be very efficient taking a long time, largely depend on the ability of the individuals who are subject to eye fatigue possibly to cause overlooking of the foreign particles so that the method relying on visual inspection is not suitable for a large number of samples or a large quantity of powdery products. Moreover, modern lines for the production of powdery resins are always operated in a closed system so that it is difficult to take samples of the resin powder at as many as desired spots in the production line. Accordingly, the intermixing conditions of foreign particles in the powdery resin product can hardly be under control on the base of the information obtained by the inspection of a limited number of samples taken from the production line.

The instrumental methods by image analysis can solve the problem due to the ability difference of individuals. Conventional optical instruments for inspection, however, have a limited width of the visual field so that the amount of the powder which can be inspected at one time is relatively small providing no solution of the problem in the visual method that the overall throughput of the product inspected by the inspection system is far from satisfactory. This situation is one of the reasons for the retarded prevalence of the instrumental inspecting methods.

In view of the above described situation and problems in the prior art, the inventors have continuedly conducted investigations for the automatization of the inspection system for the detection of colored foreign particles in polyvinyl chloride resin products and previously proposed a method and apparatus for the detection and counting of colored foreign particles and fish eyes in a continuously running film or sheet of a polyvinyl chloride resin by using a transmission-type gas-laser beam scanning detector (see Japanese Patent Kokai 58-108440). This method, however, is not applicable to the resin products in a powdery form because the laser beam has only very low transmissivity through a powder layer and is strongly reflected on the surface of the powder layer so that the results of counting inherently cannot be accurate enough and colored foreign particles alone cannot be counted selectively. In addition, the method is applied to the inspection of a powdery resin only after shaping the powdery resin into a transparent sheet or film so that the material to be inspected is subject to intermixing of foreign materials by chance in the course of shaping the powder into a film or sheet and sometimes scorched particles of the resin per se occurred in the process of shaping resulting in an inaccurate result of inspection.

SUMMARY OF THE INVENTION

The present invention accordingly has an object to provide an efficient and reliable method for the detection of colored foreign particles in a powdery polyvinyl chloride resin without the problems and disadvantages in the prior art methods.

Thus, the method of the invention for detecting colored foreign particles in a powder of a polyvinyl chloride resin comprises the steps of:
(a) eliminating static electricity from the powder by spraying ethyl alcohol thereto;
(b) continuously feeding a running transfer means of powder with the powder to form a powder layer having a uniform thickness and a flat surface on the surface of the transfer means;
(c) continuously transferring the powder layer on the transfer means below a reflection-type laser-beam detector emitting a laser beam with scanning and receiving the laser beam reflected on the surface of the powder layer; and
(d) counting the signals coming out of the detector corresponding to the number of the colored foreign particles in the powder layer.

The system of the invention for practicing the above described method comprises:
(a) a means for removing static electricity from the powder of a polyvinyl chloride resin by spraying ethyl alcohol thereto;
(b) a transfer means for continuously transferring the powder;
(c) a vibration feeder for the powder installed above the transfer means for continuously feeding the transfer means with the powder so as to form a layer of the powder on the transfer means;
(d) a reflection-type laser-beam scanning detector to project a laser beam to the surface of the layer of the powder and to receive the laser beam reflected on the surface of the layer of the powder so as to produce an output signal corresponding to the condition of the layer of the powder; and (e) a data-processing device to process the output signals from the reflection-type laser-beam scanning detector.

BRIEF DESCRIPTION OF THE DRAWING

The figure is a schematic illustration of the system in which the inventive method is practiced for the detection of colored foreign particles in a white powder of a polyvinyl chloride resin.

DETAILED DESCRIPTION OF THE PREFERRED EMBODIMENTS

In view of the problems encountered in the use of a transmission-type laser-beam detector in the above mentioned object, the inventors attempted the use of a reflection-type laser-beam detector to obtain only unsatisfactory results presumably because the reflectivity of the laser beam on the surface of the powder layer was not uniform to give no reproducible counting so that it was a provisional conclusion that this instrument was not suitable as a means of inspection in the above mentioned object.

The working principle of the reflection-type laser-beam detector is that the surface of a powder layer is scanned with a laser beam and the intensity of the reflected beam is monitored with a laser beam receiver, the output from which depends on the surface condition of the powder layer, so that a modulated output signal is obtained when the laser beam hits at a colored foreigh particle as compared with the background condition of the surface to give information on the number of the colored foreign particles scanned by the laser beam after electronic processing of the receiver output. Accordingly, it is unavoidable that the output from the receiver is not uniform even in the absence of any colored foreign particles when the surface of the powder layer is not flat and even enough. In some cases, the intensity of the reflected laser beam incident on the receiver varies so remarkably that the output signals of the receiver are counted and recorded as if there be a large number of colored foreign particles despite absence of such particles which might be responsible for the modulation of the output signals.

With an object to solve the above mentioned problem, the inventors have continued their investigations and come to an idea that the undesirable irregular reflection on the surface of the powder layer could be prevented if certain means be undertaken to remove the reasons which disturb formation of a flat and even surface of the powder layer having a uniform thickness. This idea has led the inventors to the attempts to take measures that the static electricity accumulated in the powder is eliminated as completely as possible before a transfer means of the powder such as a belt conveyor is fed with the powder, that the uniformity in the feed rate of the powder to the transfer means is ensured as far as possible over a specified width of the transfer means and that the surface of the powder layer is levelled as completely as possible before the portion arrives at just below the laser-beam scanning detector so as to ensure uniformity in the thickness and evenness or flatness of the surface of the powder layer. The present invention has been completed as a results of such investigations.

In the following, the method of the invention as well as the system therefor are described in more detail with reference to the accompanying drawing, which, however, is given merely to illustrate an embodiment of the invention..

The white resin powder 2 to be inspected according to the invention is stored in several hopper bins 1,1, ... , from which the powder 2 falls down to the service hopper 3 installed below the hopper bins 1 in such a freely movable fashion as to receive the powder 2 flowing down from the discharge ports of the respective hopper bins 1. The bottom of the service hopper 3 opens above the continuous feeding means 4 such as a vibration feeder which feeds the transfer means 5 such as a belt conveyor with the powder 2 at a controlled rate. Thus, the powder 2 stored in each hopper bin 1 is sent to the transfer means 5 at a controlled rate to form a powder layer having a uniform thickness and fully flat and even surface. The type of the vibration feeder 4 is not particularly limitative and machines of any types conventionally used in powder feeding can be used here although it is preferably an electromagnetic vibration feeder.

The vibration feeder 4 works preferably at an amplitude of 0.1 to 0.6 mm or, more preferably, 0.2 to 0.4 mm and at a frequency of 500 to 600 Hz so as to spread the powder flow falling from the feed end 4a over a specified width of the transfer means 5, e.g., belt conveyor, to form a powder layer thereon having a thickness as uniform as possible. The vibration amplitude of the vibration feeder 4 should not be too large, especially, when the powder 2 is a powdery polyvinyl chloride resin because the up-and-down movement of the resin particles on the feeder trough is unduly increased by the vibrating movemebt of the feeder 4 with an excessibly large amplitude also to disadvantageously increase generation and accumulation of static electricity by the frictional contacting of the particles with each other.

Facing the down flow of the powder 2 coming out of the feed end 4a of the vibration feeder 4, a means to eliminate the static electricity 6 is installed which serves to eliminate the static electricity carried by the powder 2. The means 6 for the elimination of static electricity can work by any one or a combination of known principles including ejection of steam, spraying of water or alcohol optionally containing a surface active agent, electric corona discharging and the like. Although the figure shows that the means 6 for the elimination of static electricity is installed facing the down flow of the powder 2 from the feed end 4a of the vibration feeder 4, it is of course optional that two or more of the means 6, which may be of the same principle or of different principles, are installed at several positions including the above mentioned one and other positions such as the inlet port of each of the hopper bins 1, above the inlet port of the service hopper 3, above the center portion of the vibration feeder 4, above the transfer means 5 and so on in order to achieve more complete elimination of the static electricity from the powder 2 at the respective positions. When the powder 2 to be inspected is highly susceptible to the accumulation of static electricity as is the case with certain synthetic resins such as powdery polyvinyl chloride resins, it is very advantageous or rather essential that an alcohol, which is preferably ethyl alcohol, is sprayed to the powder 2 before the powder 2 is introduced into each of the hopper bins 1,1, . . . and then one or more means working by different principles are undertaken at the above mentioned positions. The volume of the sprayed ethyl alcohol should preferably be in the range from 1 ml to 5 ml per kg of the powdery polyvinyl chloride resin. It is important that, when elimination of the static electricity is performed by spraying of a liquid, the amount of the sprayed liquid should be small enough so long as to be effective for the elimination of static electricity in order to avoid clamminess of the powder to cause a loss of flowability even by setting aside the economical disadvantage.

The transfer means of the powder is not limited to the above described belt conveyor but any other known means can be used here including turn tables, moving tables and the like provided that the means has a flat surface, on which the powder layer is formed, and without joints. It is further desirable that the top surface of the belt and table on which the layer of the white or lightcolored powder is formed has a color as close as possible to the color of the powder. When the transfer means 5 is a belt conveyor as is illustrated in the drawing, it is advantageous to provide a supporting table 7 having a flat and smooth surface on which the belt of the conveyor 5 runs after receiving the powder 2 flowing down from the feed end 4a of the vibration feeder 4 to form a powder layer thereon in order to minimize the vibration of the belt in the vertical direction. It is sometimes advantageous to provide a scraper 8 above the transfer means 5 at a position between the falling point of the down-flow of the powder 2 and the detector 11 in order to level the surface of the powder layer more completely to impart a uniform thickness.

The thickness of the powder layer thus formed on the transfer means 5 is smaller than 2 mm or, preferably, in the range from 0.7 to 1.5 mm though dependent on the desired accuracy of detection. A smaller thickness of the powder layer gives a higher accuracy of detection due to the decrease in the number of overlooked colored foreign particles embedded in the powder layer. The thickness of the powder layer can be easily controlled by adjusting the feed rate from the vibration feeder 4 and the running velocity of the transfer means 5.

The powder layer formed on the transfer means 5 is then transferred below a reflection-type laser-beam scanning detector 11 installed above the transfer means 5. The detector 11 is composed of a laser beam scanner 9 and a laser beam receiver 10. The laser is preferably a gas laser such as a helium-neon gas laser. Though not illustrated in the figure, the laser beam scanner 9 is constructed from a gas laser as an emitter of the laser beam, lens system for fine control of the diameter of the beam spot, rotatable polygonal mirror, start-pulse unit and other parts and the laser beam receiver 10 has a mirror box, photomultiplier and others.

The laser beam preferably has a wavelength of 1000 nm or smaller and the output of the laser is preferably 10 mW or smaller in order to avoid any possible temperature elevation and chemical changes of the powder 2 under inspection by absorbing the energy of the laser beam. An example of suitable gas lasers is a heliumneon gas laser emitting a beam at a wavelength of 632.8 nm with an output of 5 mW.

The laser beam emitted from the scanner 9 is imparted with a controlled diameter by means of the lens system. The diameter is preferably in the range from 50 $\mu$m to 200 $\mu$m. The laser beam projected on to the surface of the powder layer is scanned in the transverse direction of the powder layer on the transfer means by means of the rotating polygonal mirror which deflects the laser beam. The frequency of scanning is preferably in the range from 2000 Hz to 3000 Hz and the amplitude of scanning should be sufficient to cover the whole width of the powder layer in the transverse direction. The laser beam is received in the start pulse unit and the reflection of the beam on the surface of the powder layer is received in the laser beam receiver 10 in which the photomultiplier serves for the photoelectric conversion of the laser beam to transmit the electric signals proportional to the intensity of received light to a control board 12. The scanning laser beam received in the start pulse unit serves as a reference in the trans-verse direction of the powder layer.

When a colored foreign particle on the moving layer of the white powder 2 on the transfer means 5 receives and reflects the laser beam, a great modulation is caused in the intensity of the light received in the receiver 10 as compared with the reflection on the white powder as the background. Thus modulated electric output signals from the photomultiplier are transmitted to the control board 12 where the signals are converted into differential signals. Namely, the differential signals produced in the control board have a peak corresponding to each of the colored foreign particles under scanning with the laser beam and the number of such peaks is recorded as the number of the defect spots in the powder layer. The detection level of the differential signals set, for example, in the range from 2.00 to 9.99 volts.

The above mentioned detection level of the differential signals is preset depending on the desired minimum size of the colored foreign particles to be detected. Thus, it is possible to count the number of the colored foreign particles alone having a size to exceed a certain lower limit by intentionally overlooking smaller particles provided that the correlation between the size of the colored foreign particles and the peak height of the differential signals is determined in advance. Though dependent on the performance of the instrument, it is easy to dectect colored foreign particles having a diameter of 0.1 mm or larger in a pure white powder of a polyvinyl chloride resin.

As is mentioned before, it is essential that the moving powder layer on the transfer means 5 has a surface as even or flat as possible because otherwise the intensity of the reflected laser beam is subject to an irregular fluctuation so that the background level of the differential signals in the control board 12 also fluctuates to decrease the sensitivity of detection or to cause a miscounting or overcounting including the false peak signals produced in the absence of any colored foreign particles.

When the detector system of the invention is adequately designed, the width of the powder layer on the transfer means 5 can be as large as 100 mm or even larger and the transfer velocity of the powder layer can be up to 15 meter/minute so that the overall throughput of inspection can be 150 kg/hour or larger assuming that the powdery material under inspection is a white poly-vinyl chloride resin although the capacity of the system largely depends on the desired detection level of the colored foreign particles. In an example, a time of 5 to 10 minutes is sufficient for the full inspection of 5 to 7 kg of a powdery polyvinyl chloride resin.

It is optional that a pulse-generating roller 13 is installed above the transfer means 5 in the vicinity of the forward end, which serves to detect the moving velocity of the transfer means 5 with an object to control the time lag possibly occurring in the counting of the colored foreign particles in the laser beam scanning detector. Namely, the information relative to the transverse direction of the powder layer is obtained in the laser beam scanning detector 11 and the information relative to the moving direction of the powder layer is obtained in this pulse-generating roller 13. The information is transmitted to the control board 12 where it is processed by means of a microcomputer and exhibited on the display unit 14 as the information for the number of the colored foreign particles. The inspected powder 2 arriving at the forward end of the transfer means 5 falls down by means of scraping or suction as completely as possible and received in a discharge tank 15.

The powdery material to which the inventive method and inspection system are applicable includes a variety of white or lightcolored powders such as powdery synthetic resins, e.g., polyvinyl chloride-based resins, MBS resins, polyvinyl alcohol resins and the like having an average particle diameter of 20 to 250 μm though not particularly limitative thereto. The principle of the inventive method is particularly suitable for the inspection of powdery polyvinyl chloride resins which are notoriously susceptible to charging of static electricity.

The colored foreign particles detectable by the inventive method and detection system include those coming from a variety of origins provided that the particle has a visually detectable size of, for example, 0.1 mm or larger in diameter. In a polyvinyl chloride resin powder, colored foreign particles include those contained in the powder as polymerized, scorched particles occurring by overheating in the drying step, rust particles of metals formed on and falling off the inner walls of the equipment and pipe lines and so on.

In the following, the inventive detecting method and detection system are described in more detail by way of examples.

EXAMPLE 1

Each a 5 kg portion of a commercial product of a polyvinyl chloride resin having an average particle diameter of about 150 μm (TK 1000, a product by Shin-Etsu Chemical Co.) was blended with 10 or 20 particles of a black foreign material having a diameter of about 0.3 mm and used as the test samples together with another 5 kg portion of the same resin as obtained as the reference sample. These three samples No. 1, No. 2 and No. 3 containing no, 10 and 20 black paricles, respectively, were subjected to the inspection tests either by the conventional visual method or according to the inventive method using a detection system described below. The visual inspection was carried out by spreading the sample powder on a sheet of white paper and picking up the black particles while the powder was moved by using a spatula.

Hopper bins

Six hopper bins each having a capacity of 15 liters installed in a rotary arrangement Service hopper 15 liter capacity Vibration feeder Electromagnetic type, vibrating at 50 Hz with an amplitude of about 0.3 mm, 230 mm by 420 mm trough Transfer means Jointless belt conveyor, white, 400 mm wide and 3.8 m long, running velocity 6 meters/minute, width of powder layer about 230 mm, thickness of the powder layer about 1.0 mm Reflection-type gas laser beam scanning detector Flying-spot reflected light receiver, helium-neon gas laser emitting at a wavelength of 632.8 nm, output 5 mW, amplitude of oscillating laser beam scanning 200 mm, spot size 0.1 mm in diameter, scanning frequency 3000 Hz Setting of detection level Range 2.00 to 9.99 volts, defect signals corresponding to the size of the colored foreign particles shown below according to the preparatory experiments for setting

| Signal of defects | Size of colored particle |
| --- | --- |
| 7 volts or larger | 0.3 mm or larger |
| 5 to 7 volts | 0.2 to 0.3 mm |
| 4 to 5 volts | 0.1 to 0.2 mm |

Elimination of static electricity

Ethyl alcohol sprayed in a volume of about 10 ml per 5 kg of the polyvinyl chloride resin before introduction into the hopper bins, three rod-type corona dischargers each having an input capacity of 17 VA used concurrently Table 1 below summarizes the number of the detected black particles and the time taken for the inspection in each of the inspection tests. As is shown in this table, the method of the invention is very advantageous in respect of the rapidness taking only one fourth to one fifth of that taken in the visual method.

TABLE 1

| Method | Sample No. | Number of detected particles | Time taken for inspection |
| --- | --- | --- | --- |
| Inventive(*) | 1 | 0 | 390 seconds |
|  | 2 | 8 | 378 seconds |
|  | 3 | 17 | 380 seconds |
| Visual | 1 | 0 | 30 minutes |
|  | 2 | 8 | 36 minutes |
|  | 3 | 19 | 33 minutes |

(*)Background level 3.0 volts

EXAMPLE 2

Three lots A, B, C of actual polyvinyl chloride resin products each in a size of 20 tons were subjected to the inspection test and samples each in an amount of 5 kg were taken from the respective lots. The resins of the lots A, B and C had a bulk density of 0.543 g/ml, 0.540 g/ml and 0.542 g/ml, respectively, and powder flowability of 10.2 seconds, 10.3 seconds and 10.3 seconds, respectively, according to the testing procedures specified in JIS K 6721 for the bulk density and ASTM D-1895 for the powder flowability. The samples were subjected to the inspection tests for detecting colored foreign particles having a diameter of 0.1 mm or larger either by the conventional visual method or by the inventive instrumental method to give the results shown in Table 2 below. The inventive instrumental inspection was performed by using the same detection system as in Example 1 operated under substantially the same conditions. Table 2 also includes the results obtained in a comparative test in which the same procedure as in the inventive method was repeated for the lot A excepting omission of spraying of ethyl alcohol. In this case, the number of the particle counting was remarkably large, especially, for the signals corresponding to the particles of 0.1 to 0.2 mm diameter presumably due to the irregularity of the surface of the powder layer to cause false counting signals.

TABLE 2

| Method | Lot | Number of detected particles, size in mm | | | Time taken for inspection |
|---|---|---|---|---|---|
| | | >0.3 | 0.2–0.3 | 0.1–0.2 | |
| Inventive | A | 4 | 6 | 11 | 390 seconds |
| | B | 2 | 2 | 35 | 403 seconds |
| | C | 10 | 5 | 5 | 396 seconds |
| Comparative | A | 3 | 5 | 46 | 448 seconds |
| Visual | A | 5 | 8 | 1 | 43 minutes |
| | B | 3 | 3 | 38 | 41 minutes |
| | C | 12 | 4 | 8 | 45 minutes |

What is claimed is:

1. A method for detecting colored foreign particles in a powder of a polyvinyl chloride resin which comprises the steps of:
   (a) eliminating static electricity from the powder by spraying ethyl alcohol thereto;
   (b) continuously feeding a running transfer means of powder with the powder to form a powder layer having a uniform thickness and a flat surface on the surface of the transfer means;
   (c) continuously transferring the powder layer on the transfer means below a reflection-type laser-beam detector emitting a laser beam with scanning and receiving the laser beam reflected on the surface of the powder layer; and
   (d) counting the output signals coming out of the detector corresponding to the number of the colored foreign particles in the powder layer.

2. The method as claimed in claim 1 wherein the volume of ethyl alcohol sprayed to the powder of a polyvinyl chloride resin is in the range from 1 ml to 5 ml per kg of the powder.

3. The method as claimed in claim 1 wherein the powder layer formed in step (b) has a thickness in the range not exceeding 2 mm.

4. The method as claimed in claim 1 wherein the laser beam has a wavelength not exceeding 1000 nm.

5. A system for the detection of colored foreign particles in a powder of polyvinyl chloride resin which comprises:
   (a) a means for removing static electricity from the powder of a polyvinyl chloride resin by spraying ethyl alcohol thereto;
   (b) a transfer means for continuously transferring the powder;
   (c) a vibration feeder for the powder installed above the transfer means for continuously feeding the transfer means with the powder so as to form a layer of the powder on the transfer means;
   (d) a reflection-type laser-beam scanning detector to project a laser beam to the surface of the layer of the powder and to receive the laser beam reflected on the surface of the layer of the powder so as to produce an output signal corresponding to the condition of the layer of the powder; and
   (e) a data-processing device to process the output signals from the reflection-type laser-beam scanning detector.

6. The system for the detection of colored foreign particles in a powder of a polyvinyl chloride resin as claimed in claim 5 wherein the reflection-type laser-beam scanning detector has a helium-neon gas laser.

* * * * *